US007420064B2

(12) United States Patent
Luinstra et al.

(10) Patent No.: US 7,420,064 B2
(45) Date of Patent: Sep. 2, 2008

(54) CATALYST AND METHOD FOR THE CARBONYLATION OF OXIRANES

(75) Inventors: Gerrit Luinstra, Mannheim (DE); Ferenc Molnar, Speyer (DE); Bernhard Rieger, Oberelchingen (DE); Markus Allmendinger, Deggingen (DE)

(73) Assignee: BASF SE (DE)

( * ) Notice: Subject to any disclaimer, the term of this patent is extended or adjusted under 35 U.S.C. 154(b) by 279 days.

(21) Appl. No.: 10/523,263

(22) PCT Filed: Jul. 31, 2003

(86) PCT No.: PCT/EP03/08479

§ 371 (c)(1),
(2), (4) Date: Mar. 7, 2005

(87) PCT Pub. No.: WO2004/012860

PCT Pub. Date: Feb. 12, 2004

(65) Prior Publication Data

US 2005/0256320 A1    Nov. 17, 2005

(30) Foreign Application Priority Data

Aug. 1, 2002    (DE) ................. 102 35 317

(51) Int. Cl.
*C07D 305/12* (2006.01)
*B01J 31/00* (2006.01)
(52) U.S. Cl. ............................ 549/328; 502/152
(58) Field of Classification Search ............ 549/328; 502/152
See application file for complete search history.

(56) References Cited

U.S. PATENT DOCUMENTS

| 3,260,738 | A | 7/1966 | McClure et al. |
| 4,620,033 | A | 10/1986 | Isshiki et al. |
| 5,310,948 | A | 5/1994 | Drent et al. |
| 5,731,402 | A | 3/1998 | Nishida et al. |
| 6,084,124 | A | 7/2000 | Slaugh et al. |

FOREIGN PATENT DOCUMENTS

| EP | 0 577 206 | 1/1994 |
| EP | 0 688 806 | 12/1995 |
| GB | 1020575 | 2/1966 |
| JP | 9169 753 | 6/1997 |
| WO | WO-02/12161 | 2/2002 |
| WO | WO-03/050154 | 6/2003 |
| WO | WO-2004/012861 | 2/2004 |

OTHER PUBLICATIONS

Allmendinger et al., Z. Anorg. Allg. Chem., 2003, 629:1347-1352.*
Furukawa et al., "Copolymerization of Carbon Monoxide with Alkylene Oxide", *Die Makromolekulare Chemie*, vol. 89, pp. 263-268 (1965).
Kamiya et al., "The Reaction Of Small Ring Compound With Carbon Monoxide The Carbonylation Of Oxirane", *Chemistry Letters*, pp. 1549-1552 (1980).
Kowalczuk et al., "Synthesis Of New Glycidyloxypropiolactones", *Polish Journal Of Chemistry*, vol. 55, pp. 1965-1967 (1981).
Rossiter, "Synthetic Aspects and Applications of Asymmetric Epoxidation", *Asymmetric Synthesis*, vol. 5, pp. 193-246 (1985).
Finn et al., "On the Mechanism of Asymmetric Epoxidation with Titanium—Tartrate Catalysts", *Asymmetric Synthesis*, vol. 5, pp. 247-308 (1985).
Gao et al., "Catalytic Asymmetric Epoxidation and Kinetic Resolution: Modified Procedures Including in Situ Derivatization", *J. Am. Chem. Soc.*, vol. 109, pp. 5765-5780 (1987).
Schreiber et al., "Application of the Two-Directional Chain Synthesis Strategy to the First Stereochemical Assignment of Structure to Members of the Skipped-Polyol Polyene Macrolide Class: Mycoticin A and B", *J. Am. Chem. Soc.*, vol. 109, pp. 8120-8122 (1987).
Jacobsen et al., "Enantioselective Catalytic Ring Opening of Epoxides with Carboxylic Acids", *Tetrahedreon Letters*, vol. 38, No. 5, pp. 773-776 (1997).
Furrow et al., "Practical Access to Highly Enantioenriched C-3 Building Blocks via Hydrolytic Kinetic Resolution", *J. Org. Chem.*, vol. 63, pp. 6776-6777 (1998).
Jacobsen, "Asymmetric Catalysis of Epoxide Ring-Opening Reactions", *Acc. Chem. Res.*, vol. 33, pp. 421-431 (2000).
Lee et al., "Synthesis of β-Lactones by the Regioselective, Cobalt and Lewis Acid Catalyzed Carbonylation of Simple and Functionalized Epoxides", *J. Org. Chem.*, vol. 66, pp. 5424-5426 (2001).
Getzler et al., "Synthesis of β-Lactones: A Highly Active and Selective Catalyst for Epoxide Carbonylation", *J. Am. Chem. Soc.*, vol. 124, No. 7, pp. 1174-1175 (2002).
Mahadevan et al., "[Lewis Acid]$^+$[Co(CO)$_4$]$^-$ Complexes: A Versatile Class of Catalysts for Carbonylative Ring Expansion of Epoxides and Aziridines", *Angew. Chem. Int. Ed.*, vol. 41, No. 15, pp. 2781-2784 (2002).
Molnar et al., "Multisite Catalysis: A Mechanistic Study of β-Lactone Synthesis from Epoxides and CO—Insights into a Difficult Case of Homogeneous Catalysis", *Chem. Eur. J.*, vol. 9, No. 6, pp. 1273-1280 (2003).

* cited by examiner

*Primary Examiner*—Rei-Tsang Shiao
(74) *Attorney, Agent, or Firm*—Connolly Bove Lodge & Hutz LLP

(57) ABSTRACT

Lactones are prepared by catalytic carbonylation of oxiranes using a catalyst system comprising
a) at least one cobalt compound as component A and
b) at least one metal compound of the formula (I) as component B, $$MX_xR_{n-x} \qquad (I)$$

where
M is an alkaline earth metal or a metal of group 3, 4 or preferably 12 or 13 of the Periodic Table of the Elements,
R is hydrogen or a hydrocarbon radical which may be substituted on the carbon atoms other than the carbon atom bound to M,
X is an anion,
n is a number corresponding to the valence of M and
x is in the range from 0 to n,
with n and x being selected so that the compound is uncharged, as catalyst.

9 Claims, No Drawings

CATALYST AND METHOD FOR THE CARBONYLATION OF OXIRANES

RELATED APPLICATIONS

This application is a national stage application (under 35 U.S.C. 371) of PCT/EP2003/008479 filed Jul. 31, 2003 which claims benefit to German application Ser. No. DE 102 35 317.4 filed Aug. 1, 2002.

The present invention relates to the preparation of lactones by catalytic carbonylation of oxiranes in the presence of a catalyst system, to a corresponding catalyst system and to its use.

The catalytic carbonylation of simple and substituted oxiranes is known per se. The products are often riot the desired lactones, or the reaction conditions or the starting materials do not permit efficient preparation or isolation of lactones. The compounds can frequently be obtained by means of complicated and costly syntheses.

JP-A-09 169 753 describes the carbonylation of epoxides to lactones over $Co_2(CO)_8$ as catalyst in a flow-through reactor. The conversions are only 30%. This means that a separation and recirculation facility is required to achieve a high yield and purity of the lactone.

GB-A-1,020,575 relates to a process for preparing polymers of β-lactones. Carbon monoxide and a 1,2-epoxide are reacted to form a β-lactone as intermediate. This is carried out using octacarbonyldicobalt as catalyst. In addition, it is possible to use a promoter selected from among metal halides such as potassium iodide and quaternary ammonium halides such as tetraethylammonium bromide. However, the yields of lactone are less than 10% and the main fractions of the products are polyhydroxypropionic esters. In addition, the reaction is carried out in a complicated manner using a plurality of pressure stages.

EP-B-0 577 206 relates to the carbonylation of epoxides over a catalyst system comprising a cobalt source and a hydroxy-substituted pyridine compound, in particular 3-hydroxypyridine or 4-hydroxypyridine. The carbonylation is preferably carried out in the presence of a hydroxy compound such as water or alcohols. The activities of the catalysts used are relatively low, and isolation of the lactones is not described. It has also been observed that a change in the reaction mixture occurs after the carbonylation has ended. Over a period of 24 hours, polymerization of the lactone takes place. This indicates that the lactone is not unreactive in the reaction mixture. It is also known that lactones can polymerize in the presence of pyridines.

Chemistry Letters 1980, pages 1549 to 1552, relates to the reaction of epoxides with carbon monoxide over a rhodium complex as catalyst. The yields are not more than 70%.

J. Org. Chem. 2001, 66, pages 5424 to 5426, describes the synthesis of β-lactones by carbonylation of epoxides over cobalt and Lewis acid catalysts. A system comprising PPNCo(CO)$_4$ and $BF_3.Et_2O$ is used as catalyst. The yields are in the range from 7 to 86%. However, the reaction time is from 7 to 24 hours, and the use of large amounts of catalyst is necessary.

J. Am. Chem. Soc. 124, No. 7, 2002, pages 1174 to 1175, describes the preparation of β-lactones by carbonylation of epoxides. The catalyst used is a mixture of a salt of aluminum salts and a tetracarbonylcobaltate. The handling and synthesis of the aluminum compound are complicated, so that the process cannot be carried out on a large industrial scale.

It is an object of the present invention to provide an uncomplicated and efficient process for preparing lactones by carbonylation of epoxides. A further object is to provide a suitable catalyst system for this reaction.

We have found that this object is achieved by a process for preparing lactones by catalytic carbonylation of oxiranes, wherein a catalyst system comprising
a) at least one cobalt compound as component A and
b) at least one metal compound of the formula (1) as component B, $$MX_xR_{n-x} \tag{I}$$

where
M is an alkaline earth metal or a metal of group 3, 4 or preferably 12 or 13 of the Periodic Table of the Elements,
R is hydrogen or a hydrocarbon radical which may be substituted on the carbon atoms other than the carbon atom bound to M,
X is an anion.
n is a number corresponding to the valence of M and
x is in the range from 0 to n,
with n and x being selected so that the compound is uncharged, is used as catalyst.

The object of the invention is also achieved by a catalyst as defined above except for the combination $Al(C_2H_5)_3/Co(acac)_3$.

The catalyst system $Al(C_2H_5)_3/Co(acac)_3$ has already been described in Die Makromolekulare Chemie 89, 1965, pages 263 to 268. This reference is concerned with the copolymerization of carbon monoxide with alkylene oxides and does not describe the formation of lactones.

Lactones are valuable compounds for preparing biodegradable polyesters, cf., for example, EP-A-0 688 806. These polyesters are widely used, for example as polyols in polyurethane production or as material of construction.

According to the present invention, it has been found that a combination of cobalt compounds, in particular compounds in a low oxidation state, and metal compounds forms an efficient catalyst system for the carbonylation of oxiranes to lactones under mild conditions.

In the catalyst system used according to the present invention, preference is given to 0.1 to 1000 mol, particularly preferably from 1 to 100 mol, of component B being present per mole of component A.

The component A is preferably selected so that a cobalt carbonyl compound is present under the reaction conditions. This means that a cobalt carbonyl compound can be used directly as component A or it is possible to use a compound which is converted into a cobalt carbonyl compound under the reaction conditions.

R is preferably hydrogen or $C_{1-32}$-alkyl, $C_{2-20}$-alkenyl, $C_{3-20}$-cycloalkyl, $C_{6-18}$-aryl, $C_{7-20}$-aralkyl or $C_{7-20}$-alkaryl, with substituents being able to be present on the carbon atoms other than the carbon atom bound to M. R is preferably hydrogen or a monoanionic hydrocarbyl group, for example $C_{1-32}$-alkyl such as methyl, ethyl, i- or n-propyl, i-, n- or t-butyl, n-pentyl or n-hexyl, $C_{2-20}$-alkenyl such as propenyl or butenyl, $C_{3-20}$-cycloalkyl such as cyclopropyl, cyclobutyl, cyclopentyl, cyclopentadienyl or cyclohexyl, $C_{6-18}$aryl such as phenyl or naphthyl, or $C_{7-20}$-arylalkyl, e.g. benzyl (the hydrocarbyl group is preferably alkyl and particularly preferred hydrocarbyl groups are methyl or ethyl), X is an anion such as halide (apart from fluoride), sulfonate, oxide, $C_{1-32}$-alkoxide, amide; with preferred anions being halide or alkoxide, particularly preferably chloride or $C_{1-12}$-alkoxide, and n corresponds to the oxidation state OS or the valence of the metal and x is smaller than or equal to n and is not negative (for each oxide ligand, x=x+1).

The component B is preferably $AlCl_xR_{3-x}$ where x is from 0 to 3 and R is $C_{1-6}$-alkyl. The numbers n and x can be integers or fractions. Fractions can arise in the case of a mixture of such compounds.

If desired, component A or B may also have an uncharged donor L bound in its coordination sphere. A donor L is in general an uncharged compound containing oxygen, nitrogen or phosphorus atoms, e.g. ethers, carbonates, ketones, sulfoxides, amines, amides, phosphines, nitro functions or nitrile functions, etc. Olefins and aromatics are also possible as donors L.

Of course, it is also possible to use mixtures of a plurality of different components B and/or A as catalyst system.

Particular preference is given to a combination of octacarbonyldicobalt and trimethylaluminum or octacarbonyldicobalt and tri ethyl aluminum or octacarbonyldicobalt and tri (sec-butyl)aluminum, or octacarbonyldicobalt and triisopropoxyaluminum.

The carbonylation is generally carried out under superatmospheric pressure and at elevated temperature. However, product formation is also observed at a carbon monoxide pressure of one atmosphere. The pressure is generally generated by means of CO gas. In particular cases, the pressure can also be partially generated by means of an inert medium such as argon or nitrogen. The pressures are in the range from 1 to 250 bar, preferably from 10 to 100 bar, particularly preferably from 20 to 60 bar. The reaction can generally be carried out at from −10 to 200° C. The preferred temperature range is from 20 to 150° C., particularly preferably from 40 to 110° C.

The carbonylation of epoxides can be carried out either batchwise or in a continuous process. It can be carried out either in the gas phase or in an inert reaction medium. This medium is generally a liquid. Suitable liquids are customary solvents such as ethers, diglyme, triglyme, tetraglyme, tetrahydrofuran, dimethoxyethane, hydrocarbons such as hexane, octane, isopar, benzene, toluene, xylene decalin; chlorinated hydrocarbons such as dichloromethane; dichloroethane, dichlorobenzene or polar solvents such as DMF, DMSO, esters, nitriles, nitro compounds, ketones or ionic liquids. Preferred solvents are DME, diglyme, dichloromethane. The oxirane can also be used as reaction medium.

To activate the catalyst system further, it is possible to add donor ligands such as phosphines or nitriles. Application of the catalyst components (e.g. cobalt and alkyl compound) to a particulate support material, e.g. silica or aluminum oxide, makes it possible to carry out the reaction in the absence of solvent as a gas-phase carbonylation.

Suitable oxirane compounds are ethylene oxide and substituted epoxides. These are usually compounds having the formula (II):

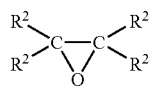

(II)

In this formula, the radicals $R^2$ are each, independently of one another, hydrogen, halogen, a nitro group —$NO_2$, a cyano group —CN, and ester group —$COOR^3$ or a hydrocarbon group having from 1 to 32 carbon atoms which may be substituted. The radicals $R^2$ in a compound (II) can all be the same, some of them can be the same or they can be four different radicals. $R^3$ can be $C_{1-12}$-alkyl or aryl.

Use is preferably made of geminally substituted epoxides, particularly preferably epoxides substituted only in the 1 position.

Examples of suitable hydrocarbon groups are $C_{1-32}$-alkyl such as methyl, ethyl, i- or n-propyl, i-, n- or t-butyl, n-pentyl or n-hexyl, $C_{2-20}$-alkenyl such as propenyl or butenyl, $C_{3-20}$-cycloalkyl such as cyclopropyl, cyclobutyl, cyclopentyl or cyclohexyl, $C_{6-18}$-aryl such as phenyl or naphthyl, and $C_{7-20}$-arylalkyl, e.g. benzyl. It is also possible for two radicals $R^2$ located on different carbon atoms of the epoxy group to be joined to one another so as to form a $C_{3-20}$-cycloalkylene group.

Substituents which may be present on the $C_{1-32}$-hydrocarbon group or R above can be, in particular, the following groups: halogen, cyano, nitro, thioalkyl, tert-amino, alkoxy, aryloxy, arylalkyloxy, carbonyldioxyalkyl, carbonyldioxyaryl, carbonyldioxyarylalkyl, alkoxycarbonyl, aryloxycarbonyl, arylalkyloxycarbonyl, alkylcarbonyl, arylcarbonyl, arylalkylcarbonyl, alkylsulfinyl, arylsulfinyl, arylalkylsulfinyl, alkylsulfonyl, arylsulfonyl and arylalkylsulfonyl.

The oxirane compound used is preferably ethylene oxide, propylene oxide, butylene oxide (1-butene oxide, BuO), cyclopentene oxide, cyclohexene oxide (CHO), cycloheptene oxide, 2,3-epoxypropyl phenyl ether, epichlorohydrin, epibromohydrin, i-butene oxide (IBO), styrene oxide or an acryl oxide. Particular preference is given to using ethylene oxide (EO), propylene oxide (PO), butylene oxide or i-butene oxide, very particularly preferably ethylene oxide or propylene oxide or a mixture thereof.

The oxirane compounds to be used for the process of the present invention can be obtained, for example, by epoxidation of terminal olefins using methods known to those skilled in the art. If the epoxidation occurs stereounspecifically, resolution of the racemate has to be carried out. Methods of resolving racemates, e.g. by means of HPLC chromatography using a chiral column material, are known to those skilled in the art. The oxirane compound is advantageously prepared directly in enantiomerically pure or optically enriched form from a terminal olefin by means of established stereoselective processes. A suitable process is, for example, the Sharpless epoxidation (cf. J. Am. Chem. Soc. 1987 (109), p. 5765 ff. and 8120 ff.; and "Asymmetric Synthesis", Edited by J. D. Morrison, Academic Press, New York, 1985, Volume 5, Chapters 7 and 8).

Furthermore, optically enriched oxirane compounds can be obtained from terminal olefins or racemic terminal epoxides by the methods described in Jacobsen et al., Tetrahedron Lett. 1997, 38, pages 773 to 776; and J. Org. Chem. 1998, 63, pages 6776 to 6777, which are also simple to carry out on a large industrial scale (see also Acc. Chem. Res. 2000, 33, pages 421 to 431).

It is also possible to prepare optically enriched oxirane compounds by mixing an appropriate amount of the racemate with the enantiomerically pure oxirane compound.

As compounds having a terminal double bond, it is in principle possible to use all olefins of this class of compound, e.g. propene, 1-butene, 1-pentene, 1-hexene, 1-heptene or 1-octene.

In general, the cobalt complexes (A) and the, for example, alkyl compounds (B) are firstly introduced into the reaction vessel either individually, simultaneously or in premixed form, if appropriate with cooling. It is also possible, if desired, for the oxirane compound to be mixed into the solution/suspension of the catalyst components before the latter is transferred to the reaction vessel. Furthermore, the oxirane compound can also be introduced directly into the reaction vessel. The carbonylation is preferably carried out under inert conditions, i.e. in the absence of moisture and air.

Termination of the reaction and separation and purification of the lactones can be carried out by generally known methods. For example, the lactone can be isolated in a simple fashion by distillation or crystallization.

The process of the present invention enables 3-hydroxypropiolactones to be obtained from the corresponding enantiomerically pure oxirane compounds. If these oxirane compounds are used in optically enriched form, lactones in which the degree of optical purity corresponds directly to the degree in the oxirane are obtained. Lactones prepared in this way can be used to establish the thermoplastic property profile of the biodegradable polymers, whose properties can be set very simply and specifically for desired applications.

The advantages of the invention can be seen in the simple operation and in the high activity and productivity of the carbonylation catalysts and the commercially available catalyst components.

The present invention also provides a process for preparing the catalyst used according to the present invention by mixing the components A und B. The invention further relates to the use of the catalyst in carbonylation reactions.

Reagents

The reagents used came from Fluka, Aldrich or Merck and were used without further purification. The solvents were dried over molecular sieves and in each case degassed before use. The aluminum alkyl compounds were used as solutions in toluene.

Analysis

NMR spectra were recorded on a Bruker AMX400 spectrometer. The IR measurements (KBr or directly as solution) were carried out on Bruker IFS 113V and IFS 66V instruments. For on-line IR studies to determine the reaction kinetics, a ReactIR™ (SiComp™ Dippersystem) from Mettler Tolede in a 250 ml Büchi reactor was employed.

General Procedure:

The desired amount of epoxide (cf. Tables 1 to 4) was added to octacarbonyldicobalt $Co_2(CO)_8$ (1 eq.) in diglyme at 0° C. under an argon atmosphere. A compound of type B (1-6 eq.) was finally added (cf. Tables 1 to 4).

To charge the steel autoclave (100 or 250 ml), it was firstly evacuated and then charged under a countercurrent of argon. After the starting materials had been transferred to the steel autoclave, a carbon monoxide pressure of 10-65 bar was set and the carbonylation mixture was maintained at 75-105° C. for a prescribed period. The carbonylation was stopped by reducing the pressure to ambient pressure, and the reaction solution obtained was cooled to 0° C., taken from the autoclave and analyzed. To separate off the catalyst, the resulting solution can be introduced into a mixture of diethyl ether/pentane. The catalyst and traces of polymer are separated off by filtration through silica gel, and subsequent fractional distillation of the filtrate gives the lactone in pure form.

Die Erfindung wird durch die nachstehenden Beispiele näher erläutert.

EXAMPLES

Example 1

Octacarbonyldicobalt $Co_2(CO)_8$ (260 mg) is dissolved in 16 ml of diglyme, the solution is cooled to 0° C. and 8 ml of propylene oxide are added. After addition of 0.77 ml of 2N solution of $Me_3Al$ in toluene, the reaction mixture is transferred in the absence of moisture and oxygen to a 100 ml steel autoclave provided with a glass liner. The carbonylation reaction is carried out at 75° C. under 60 bar of CO for 5 hours. The carbonylation reaction is stopped by reducing the pressure to ambient pressure and cooling to 0° C. Analysis ($^1$H- and $^{13}$C-NMR) of a sample indicates complete carbonylation of the epoxide and a lactone yield of >95% (by-products are polyhydroxybutyrate and acetone).

Example 2

In a 250 ml steel autoclave provided with an IR probe, octacarbonyldicobalt $Co_2(CO)_8$ (780 mg) are dissolved in 50 ml of diglyme at 0° C. under argon, and 26 ml of propylene oxide are added. After addition of 7 ml of a 2N solution of $Me_3Al$ in toluene, the autoclave is pressurized with 60 bar of CO. The carbonylation reaction is carried out at 95° C. under 60 bar of CO for 2 hours. The carbonylation reaction is stopped by reducing the pressure to ambient pressure and cooling to 0° C. Analysis ($^1$H- and $^{13}$C-NMR) of a sample indicates complete carbonylation of the epoxide and a lactone yield of >95% (by-products are polyhydroxybutyrate and acetone).

Example 3

In a 250 ml steel autoclave provided with an IR probe, octacarbonyldicobalt $Co_2(CO)_8$ (780 mg) are dissolved in 50 ml of diglyme at 0° C. under argon, and 26 ml of propylene oxide are added. After addition of 7 ml of a 2N solution of $Me_3Al$ in toluene, the autoclave is pressurized with 10 bar of CO. The carbonylation reaction is carried out at 75° C. under 10 bar of CO for 4 hours. To stop the reaction, the pressure is brought down to ambient pressure and the mixture is cooled to 0° C. Analysis ($^1$H- and $^{13}$C-NMR) of a sample indicates complete carbonylation of the epoxide and a lactone yield of >95% (by-products are polyhydroxybutyrate and acetone).

Example 4

Octacarbonyldicobalt $Co_2(CO)_8$ (130 mg) is dissolved in 8 ml of diglyme, the solution is cooled to 0° C. and 7 ml of butyloxirane are added. After addition of 0.39 ml of a 2N solution of $Me_3Al$ in toluene, the reaction solution is transferred in the absence of moisture and oxygen to a 100 ml steel autoclave provided with a glass liner. The carbonylation reaction is carried out at 75° C. under 60 bar of CO for 14 hours. The carbonylation reaction is stopped by reducing the pressure to ambient pressure and cooling to 0° C. Analysis ($^1$H- and $^{13}$C-NMR) of a sample indicates about 70% carbonylation of the epoxide and a proportion of lactone in the product of >75%.

Example 5

Octacarbonyldicobalt $Co_2(CO)_8$ (130 mg) and tetraethylammonium tetracarbonylcobaltate $Et_4NCo(CO)_4$ (232 mg) are dissolved in 10 ml of diglyme, the solution is cooled to 0° C. and 6 ml of propylene oxide are added. After addition of aluminum isopropoxide (i-PrO)$_3$Al, the reaction solution is transferred in the absence of moisture and oxygen to a 100 ml steel autoclave provided with a glass liner. The carbonylation reaction is carried out at 75° C. under 60 bar of CO for 16 hours. The carbonylation reaction is stopped by reducing the pressure to ambient pressure and cooling to 0° C. Analysis ($^1$H- and $^{13}$C-NMR) of a sample indicates virtually complete carbonylation of the epoxide and a lactone yield of >85% (by-products are polyhydroxybutyrate and acetone).

The following table summarizes further experiments which show that high conversions can be achieved in a short time using various combinations of cobalt compounds and component B.

TABLE 1

Variation of the Al component

| No. | Catalyst | Epoxide | Reaction conditions | Yield |
|---|---|---|---|---|
| 1 | $Co_2CO_8$ (1 eq.) $Me_3Al$ (2 eq.) | PO (160 eq.) | 75° C./60 bar of CO/ diglyme/5 h | Conversion 100% Lactone 96% |
| 2 | $Co_2CO_8$ (1 eq.) $Et_3Al$ (2 eq.) | PO (160 eq.) | 75° C./60 bar of CO/ diglyme/5 h | Conversion 100% Lactone 91% |
| 3 | $Co_2CO_8$ (1 eq.) $(i\text{-Butyl})_3\text{-Al}$ (2 eq.) | PO (160 eq.) | 75° C./60 bar of CO/ diglyme/5 h | Conversion 100% Lactone 87% |
| 4 | $Co_2CO_8$ (1 eq.) $Me_3Al$ (4 eq.) | PO (160 eq.) | 75° C./60 bar of CO/ diglyme/4 h | Conversion 100% Lactone 92% |
| 5 | $Co_2CO_8$ (1 eq.) $Me_3Al$ (6 eq.) | PO (160 eq.) | 75° C./60 bar of CO/ diglyme/3 h | Conversion 100% Lactone 88% |
| 6 | $Co_2CO_8$ (1 eq.) $EtCl_2Al$ (2 eq.) | PO (160 eq.) | 75° C./60 bar of CO/ diglyme/5 h | Conversion 100% Lactone 85% |
| 7 | $Co_2CO_8$ (1 eq.) $Et_2ClAlClEt_2Al$ (1 eq.) | PO (160 eq.) | 75° C./60 bar of CO/ diglyme/5 h | Conversion 100% Lactone 90% |
| 8 | $Co_2CO_8$ (1 eq.) MAO (2 eq.) | PO (160 eq.) | 75° C./60 bar of CO/ diglyme/20 h | Conversion 90% Lactone 80% |
| 9 | $Co_2CO_8$ (0.5 eq.) $Et_4NCo(CO)_4$ (1 eq.) $(i\text{-PrO})_3Al$ (1 eq.) | PO (120 eq.) | 75° C./60 bar of CO/ diglyme/16 h | Conversion 100% Lactone 87% |

All examples in Table 1 were carried out in a 100 ml steel autoclave provided with a glass liner; conversions and proportion of lactone were determined by NMR measurements on a sample; by-products are polyhydroxybutyrate and, in small amounts, acetone.

TABLE 2

Variation of the pressure

| No. | Catalyst | Epoxide | Reaction conditions | Yield |
|---|---|---|---|---|
| 10 | $Co_2CO_8$ (1 eq.) $Me_3Al$ (4 eq.) | PO (160 eq.) | 75° C./80 bar of CO/ diglyme/5 h | Conversion 100% Lactone 90% |
| 11 | $Co_2CO_8$ (1 eq.) $Me_2Al$ (4 eq.) | PO (160 eq.) | 75° C./60 bar of CO/ diglyme/5 h | Conversion 100% Lactone 93% |
| 12 | $Co_2CO_8$ (1 eq.) $Me_3Al$ (4 eq.) | PO (160 eq.) | 75° C./40 bar of CO/ diglyme/5 h | Conversion 100% Lactone 92% |
| 13 | $Co_2CO_8$ (1 eq.) $Me_3Al$ (4 eq.) | PO (160 eq.) | 75° C./20 bar of CO/ diglyme/5 h | Conversion 100% Lactone 91% |
| 14 | $Co_2CO_8$ (1 eq.) $Me_3Al$ (4 eq.) | PO (160 eq.) | 75° C./10 bar of CO/ diglyme/5 h | Conversion 100% Lactone 92% |

All examples in Table 2 were carried out in a 250 ml steel autoclave without glass liner and with monitoring of the reaction by IR; conversions and proportions of lactone were determined by NMR measurements on a sample; by-products are polyhydroxybutyrate and, in small amounts, acetone.

TABLE 3

Variation of the temperature

| No. | Catalyst | Epoxide | Reaction conditions | Yield |
|---|---|---|---|---|
| 15 | $Co_2CO_8$ (1 eq.) $Me_3Al$ (4 eq.) | PO (160 eq.) | 95° C./60 bar of CO/ diglyme/2 h | Conversion 100% Lactone 92% |
| 16 | $Co_2CO_8$ (1 eq.) $Me_3Al$ (4 eq.) | PO (160 eq.) | 105° C./60 bar of CO/ diglyme/1 h | Conversion 100% Lactone 91% |

All examples in Table 3 were carried out in a 250 ml steel autoclave without glass liner and with monitoring of the reaction by IR.; conversions and proportions of lactone were determined by NMR measurements on a sample; by-products are polyhydroxybutyrate and, in small amounts, acetone.

TABLE 4

Variation of the epoxide/catalyst ratio

| No. | Catalyst | Epoxide | Reaction conditions | Yield |
|---|---|---|---|---|
| 17 | $Co_2CO_8$ (1 eq.) $Me_3Al$ (2 eq.) | PO (300 eq.) | 75° C./60 bar of CO/ diglyme/10 h | Conversion 100% Lactone 92% |
| 18 | $Co_2CO_8$ (1 eq.) $Me_3Al$ (4 eq.) | PO (600 eq.) | 75° C./60 bar of CO/ diglyme/7 h | Conversion 100% Lactone 94% |
| 19 | $Co_2CO_8$ (1 eq.) $Me_3Al$ (4 eq.) | PO (1200 eq.) | 75° C./60 bar of CO/ diglyme/6 h | Conversion 80% Lactone 90% |

All examples in Table 4 were carried out in a 100 ml steel autoclave provided with a glass liner; conversions and proportions of lactone were determined by NMR measurements on a sample; by-products are polyhydroxybutyrate and., in small amounts, acetone.

We claim:

1. A process for preparing lactones which comprises catalytic carbonylating an oxirane with a catalyst system comprising
   a) at least one cobalt compound as component A and
   b) at least one metal compound of the formula (I) as component B, $$MX_xR_{n-x} \quad (I)$$

where
M Al, Mg or Zn,
R hydrogen or $C_{1-32}$-alkyl, $C_{2-20}$-alkenyl, $C_{3-20}$-cycloalkyl, $C_{6-18}$-aryl, $C_{7-20}$-aralkyl or $C_{7-20}$-alkaryl, where substituents may be present on the carbon atoms other than the carbon atom bound to M,
X Cl, Br, I, sulfonate, oxide, $C_{1-32}$-alkoxide or amide,
n is a number corresponding to the valence of M and
x is in the range from 0 to n, with n and x being selected so that the compound is uncharged,
and wherein said oxirane is ethylene oxide, propylene oxide, butylene oxide, cyclopentene oxide or cyclohexene oxide.

2. The process as claimed in claim 1, wherein the component A is selected so that a cobalt carbonyl compound is present under the reaction conditions.

3. The process as claimed in claim 1, wherein the component B is $AlCl_xR_{3-x}$ where x is from 0 to 3 and R is $C_{1-6}$-alkyl.

4. The process as claimed in claim 1, with the exception of the combination $Al(C_2H_5)_3/Co(acac)_3$.

5. A process for preparing a catalyst which comprises mixing
 a) at least one cobalt compound as component A and
 b) at least one metal compound of the formula (I) as component B, $$MX_xR_{n-x} \qquad (I)$$

where
M Al, Mg or Zn,
R hydrogen or $C_{1-32}$-alkyl, $C_{2-20}$-alkenyl, $C_{3-20}$-cycloalkyl, $C_{6-18}$-aryl, $C_{7-20}$-aralkyl or $C_{7-20}$-alkaryl, where substituents may be present on the carbon atoms other than the carbon atom bound to M,
X Cl, Br, I, sulfonate, oxide, $C_{1-32}$-alkoxide or amide,
n is a number corresponding to the valence of M and
x is in the range from 0 to n, with n and x being selected so that the compound is uncharged.

6. The process as claimed in claim 5, as defined in claim 1, wherein said at least one metal compound of the formula (I) is trimethylaluminum, triethylaluminum, tri(sec-butyl)aluminum or triisopropoxyaluminum.

7. The process as claimed in claim 5, as defined in claim 1, wherein said at least one metal compound of the formula (I) is trimethylaluminum, triethylaluminum, tri(sec-butyl)aluminum or triisopropoxyaluminum.

8. A process as claimed in claim 6, wherein said at least one metal compound of the formula (I) is trimethylaluminum, triethylaluminum, tri(sec-butyl)aluminum or triisopropoxyaluminum.

9. The process as claimed in claim 5, wherein said catalyst is not the combination $Al(C_2H_5)_3/Co(acac)_3$.

* * * * *

UNITED STATES PATENT AND TRADEMARK OFFICE
CERTIFICATE OF CORRECTION

PATENT NO. : 7,420,064 B2  Page 1 of 1
APPLICATION NO. : 10/523263
DATED : September 2, 2008
INVENTOR(S) : Gerrit Luinstra et al.

It is certified that error appears in the above-identified patent and that said Letters Patent is hereby corrected as shown below:

In Claim 6, in column 10, on lines 7-10, "as defined in claim 1, wherein said at least one metal compound of the formula (I) is trimethylaluminum, triethylaluminium, tri(sec-butyl)aluminum or triisopropoxyaluminum." should read -- wherein said at least one cobalt compound is octacarbonyldicobalt. --

Signed and Sealed this

Twenty-fifth Day of November, 2008

JON W. DUDAS
*Director of the United States Patent and Trademark Office*